United States Patent [19]
Ziérenberg et al.

[11] Patent Number: 5,871,771
[45] Date of Patent: Feb. 16, 1999

[54] MICRONIZED BIODEGRADABLE PARTICLES, PROCESS FOR PREPARING THEM AND USE THEREOF

[75] Inventors: Bernd Ziérenberg; Gojko Muacevic, both of Ingelheim am Rhein, Germany

[73] Assignee: Boehringer Ingelheim KG, Ingelheim am Rhein, Germany

[21] Appl. No.: 479,066

[22] Filed: Jun. 7, 1995

Related U.S. Application Data

[63] Continuation of Ser. No. 76,591, Jun. 14, 1993, abandoned, which is a continuation of Ser. No. 952,385, Sep. 28, 1992, abandoned, which is a continuation of Ser. No. 830,819, Feb. 4, 1992, abandoned, which is a continuation of Ser. No. 531,190, May 31, 1990, abandoned.

[30] Foreign Application Priority Data

May 31, 1989 [DE] Germany .............................. 3917617.7

[51] Int. Cl.⁶ ....................................................... A61F 2/00
[52] U.S. Cl. ........................ 424/426; 424/1.13; 424/470; 424/489
[58] Field of Search .............................. 424/476; 514/548

[56] References Cited

U.S. PATENT DOCUMENTS 4,810,697  3/1989  Speiser et al. .......................... 514/77

FOREIGN PATENT DOCUMENTS 0257915  11/1987  European Pat. Off. .

Primary Examiner—Thurman K. Page
Assistant Examiner—William E. Benston, Jr.
Attorney, Agent, or Firm—R. P. Raymond; M-E. M. Devlin; A. R. Stempel

[57] ABSTRACT

The invention relates to micronized biodegradable particles, processes for preparing them and use thereof.

7 Claims, 1 Drawing Sheet

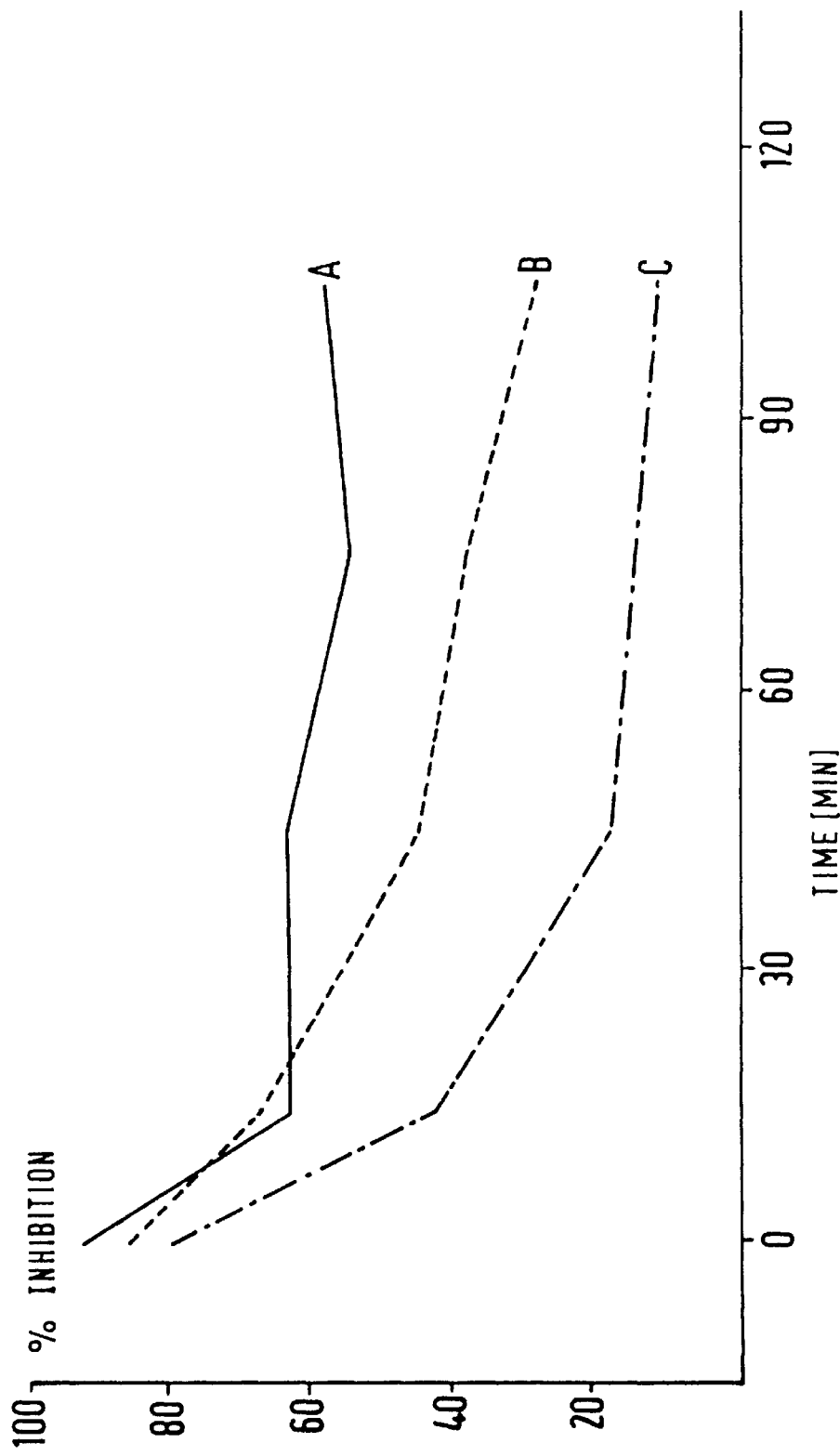

MICRONIZED BIODEGRADABLE PARTICLES, PROCESS FOR PREPARING THEM AND USE THEREOF

This is a continuation of application Ser. No. 08/076,591, filed Jun. 14, 1993, abandoned Jul. 4, 1995 which is a continuation of application Ser. No. 07/952,385, filed Sep. 28, 1992 (abandoned) Jun. 12, 1992 which is a continuation of application Ser. No. 07/930, 819, filed Feb. 4, 1992 (abandoned) Sep. 30, 1992 which is a continuation of application Ser. No. 07/531,190, filed May 31, 1990 (abandoned) Feb. 2, 1992.

1. SPECIFICATION

The invention relates to micronised biodegradable particles, processes for producing them and use thereof.

In the field of pharmaceutical compositions for inhalation, delayed release forms which release the active substance over a longer period and liberate the substance on the surface of the lungs are of particular importance.

Thus, for example, an inhaled delayed release form which ensures drug protection over a period of about 12 to 24 hours would be of particular advantage for asthmatics. To achieve-this objective, it is possible to use, in particular, active substance carriers of suitable size consisting of biodegradable polymers, the term biodegradable polymers according to the present invention meaning those polymers which are degraded on the surface of the lungs or in the human or animal body to produce pharmacologically harmless substances.

The prerequisites for the safe use of such inhaled active substance carriers are as follows:

a) the release of active substance must take place within the length of time which is medically indicated;

b) the biodegradable material of the active substance carrier must be degraded within a reasonable length of time (from the medical point of view) by the body to produce pharmacologically acceptable products; and c) the material properties of the biodegradable polymers in question must make it possible to produce active substance carriers of a size (particle diameter between about 1 and 10 $\mu$m) which enables them to be used in aerosol form.

Some suggestions for inhaled delayed release forms based on biodegradable polymeric active substance carriers are known from the prior art.

Thus, EP 257 915 discloses a delayed release form based on microcapsules which is suitable for use by inhalation, inter alia.

Similarly, EP 269 921 discloses microcapsules with a diameter in the range-from 0.1 to 10 $\mu$m, the polymeric carrier material of which is polylactide and is produced by ultrasound.

Other methods of producing microcapsules of this size are known from DE-OS 23 60 384 and 26 11 143 and from Belgian Patent 869 107. In these processes, particles are obtained having a diameter ranging from 20 to 500 nm. However, the production of active substance carriers for inhalation which are based on microencapsulated systems does have the disadvantage that it is always comparatively expensive to produce these microcapsules, in spite of numerous improvements.

When microencapsulated systems are used as carriers of pharmaceutically active substances, the following disadvantages arise, particularly with respect to the method of production:

1. a pair of solvents has to be found which will enable the formation of an emulsion, whilst both solvents must be compatible with the active substance;

2. the solvent which forms the external phase in the emulsion must also be such that it dissolves as little as possible of the active substance, which would otherwise be lost from the microcapsules;

3. it is frequently necessary to use surface-active substances as stabilisers in microencapsulation and these substances must be pharmaceutically acceptable and inert with respect to the active substance; and 4. the use of ultrasound in t he preparation of microcapsules may result in a chemical change (sonochemistry/local thermal stress) in the drug or the polymer used or other constituents of the emulsion, if the ultrasound is continued for any length of time. Furthermore, because ultrasound has been used only to a limited extent in chemistry hitherto, most of the apparatus available is suitable only for use on a laboratory scale.

Consequently, the use of methods which operate by ultrasound appears to be problematic, particularly from the point of view of production on an industrial scale.

Moreover, when the solvent or solvents is or are removed during the last step of manufacture, when spray drying is used (which is a standard procedure in the production of microcapsules) there is the danger that the active substance will be subjected to thermal damage at this stage.

Nor does the process disclosed in DE-OS 33 41 001 overcome the disadvantages, particularly as it results in so-called "nanoparticles" with a particle size of less than 1 $\mu$m. With particles of this order of magnitude there is a danger that, as a result of their low weight, caused by their small size, they will not be deposited on the surface of the lungs when used in an aerosol but will be breathed out again in a relatively short time as suspended particles without being able to release their active substance [D. Köhler, W. Fleischer and H. Matthys, Inhalation Therapy, Gedon and Reuss, Munich 1986, page 9 and cited literature, e.g. T. T. Mercer Production of Therapeutic Aerosols Principles and Techniques, CHEST 80 (1981) 813].

Moreover, these polymers have the disadvantage that they contain residues of the catalysts used in polymerisation, depending on the particular production method used. For example, in industrial processes for the ring-opening polymerisation of cyclic esters, metal salts or organometallic compounds are conventionally used as catalysts and will still be detectable in the polymer, although frequently only in tiny amounts. Consequently, if pharmaceutical preparations based on these polymers are used over long periods, there is a danger that in the course of time these catalyst residues will accumulate in individual organs or throughout the body of the person or animal concerned.

The Belgian patent referred to above additionally permits only the adsorption of active substances, with the result that the individual particles can only be charged with an amount ranging from 0.1 to 1.5% by weight and therefore a therapeutic effect can be achieved only by administering an unreasonably large amount of particles [Brasseur et al., European Journal of Cancer 16 (1980) 1441; Couvreur et al., Journal of Pharmacy and Pharmacology 31 (1979) 331; Abdel El Egakey et al., Pharmaceutica Acta Helvetica 57 (8), (1982) 236].

Furthermore, this process does not provide any way of encapsulating pharmaceutical substances which are only slightly soluble in water, since polymerisation has to be carried out in an aqueous medium which has to contain the active substance in a low concentration.

The aim of the present invention is to provide micronised particles containing active substance which are suitable for use as delayed release aerosols and which do not have the disadvantages described above.

A further objective of this invention is to propose a process for preparing the micronised active substance-containing particles according to the invention wherein, without thermal loading and/or ultrasound, a carrier material charged with active substance is brought to a particle size which enables these particles carrying the active substance to be used as a delayed release aerosol.

A further aim of the present invention is to provide micronised particles of a material which is free from catalyst residues.

The aim of the present invention is achieved by means of the biodegradable polymer charged with active substance, which is ground by jet grinding to a particle diameter in the range from 1 to 10 $\mu$m.

Suitable biodegradable polymers include all (possibly catalyst-free) polymers which have suitable crystalline properties or sufficient hardness to enable jet grinding. It is preferable to use polylactides having a molecular weight from 1000 to 10,000, poly-L(-)-lactide with a molecular weight in the range from 1000 to 5000 being particularly preferred.

The molecular weight constitutes a parameter by means of which the diffusion coefficient and hence the rate of release of the active substance can be controlled. Other parameters include the particle size distribution of the particles charged with pharmaceutically active substance and also the charging level of polymer with the active substance (see Table 3).

The preparation of a catalyst-free poly-L(-)-lactide, the molecular weight of which is within the ranges specified, is known from European Patent 261 572.

However, it is also possible to use other biodegradable polymers or copolymers provided that they have the crystalline properties which are suitable for this jet grinding process. Examples include: homo- and copolymers based on hydroxycarboxylic acids, such as polymers of glycolide, lactide, methylglycolide, dimethylglycolide, polymethylglycolide, diethylglycolide, dibutylglycolide, caprolactone, valerolactone, decalactone, propiolactone, butyrolactone, pivalolactone, as well as polymers based on trioxanone, dioxanone (1,3 and 1,4), substituted dioxanone, trimethylene carbonate, ethylene carbonate and propylene carbonate.

Other examples of suitable comonomers include: lactic acid, glycolic acid, pentaerythritol, sorbitol, adonitol, xylitol, fructose, epichlorohydrin, isopropylmorpholine, isopropylmethylmorpholinedione, β-propionic acid, tetramethylglycolide, β-butyrolactone, -butyrolactone, pivalolactone, α-hydroxybutyric acid, α-hydroxyisobutyric acid, α-hydroxyvaleric acid, α-hydroxyisovaleric acid, α-hydroxycaproic acid, α-hydroxyisocaproic acid, α-hydroxy-α-ethylbutyric acid, α-hydroxy-α-methylvaleric acid, α-hydroxyheptanoic acid, α-hydroxyoctanoic acid, α-hydroxydecanoic acid, α-hydroxytetradecanoic acid and α-hydroxystearic acid.

Suitable pharmaceutical compositions include all those for which application in aerosol form appears to be useful, such as anticholinergics, antiallergics, steroids and β-sympathomimetics. Examples include:

(a) 1-(3,5-dihydroxyphenyl)-1-hydroxy-2-[(4-hydroxyphenyl)isopropylamino]ethane (Fenoterol)

(b) 4-amino-α-[tert.-butylamino)methyl]-3,5-dichlorobenzyl alcohol (Clenbuterol)

(c) 2-hydroxymethyl-3-hydroxy-6-(1-hydroxy-2-tert-butylaminoethyl)pyridine (Pirbuterol)

(d) 8-hydroxy-5-[1-hydroxy-2-[(1-methylethyl)-amino]butyl]-2(1H)-quinolinone (Procaterol)

(e) 2-(tert.-butylamino)-1-(4-hydroxy-3-hydroxymethylphenyl)ethanol (Salbutamol)

(f) 1-(3,5-dihydroxyphenyl)-2-(tert.-butylamino)-ethanol (Terbutalin)

(g) 1-(2-fluoro-4-hydroxyphenyl)-2-[4-(1-benzimidazolyl)-2-methyl-2-butylamino]ethanol (h) erythro-5'-hydroxy-8'-(1-hydroxy-2-isopropylaminobutyl)-2H-1,4-benzoxazin-3(4H)-one (i) 1-(4-amino-3-chloro-5-trifluoromethylphenyl)-2-(tert.-butylamino)ethanol (k) 1-(4-ethoxycarbonylamino-3-cyano-5-fluorophenyl)-2-(tert.-butylamino)ethanol (l) N,N'-bis[2-(3,4-dihydroxyphenyl)-2-hydroxyethyl]-hexamethylenediamine (Hexoprenalin)

(m) 7-[3-[[2-(3,5-dihydroxyphenyl)-2-hydroxyethyl]-amino]propyl]-3,7-dihydro-1,3-dimethyl-1H-purine-2,6-dione (Reproterol)

(n) [5-[2-[(1,1-dimethylethyl)amino]-1-hydroxyethyl]-2-hydroxyphenyl]-urea (Carbuterol)

(o) 2-chloro-α-[[(1,1-dimethylethyl)-amino]methyl]-benzyl alcohol (Tulobuterol)

(p) 3-formylamino-4-hydroxy-α[N-[(1-methyl-2-p-methoxyphenyl)ethyl]-aminomethyl]benzyl alcohol semifumarate (Formoterol)

(q) N-[2-hydroxy-5-[1-hydroxy-2-[[2-(4-methoxyphenyl)-1-methylethyl]amino]ethyl]phenyl]-formamide semifumarate (r) α[(tert.butylamino)-methyl-4-hydroxy-3-(methylsulphonyl)methyl]benzyl alcohol hydrochloride (Sulfonterol)

(s) 5-[2-(tert.-butylamino)-1-hydroxyethyl]-m-phenylene-bisdimethylcarbamate) (Bambuterol)

(t) 5-[2-(tert.-butylamino)-1-hydroxyethyl]-m-phenylene-diisobutyrate (Ibuterol)

(u) 4-[2-(tert.-butylamino)-1-hydroxyethyl]-1,2-phenylene-di-4-toluate (Bitolterol)

(v) 4-hydroxy-α[[(6-(4-phenylbutoxy))hexylamino]-methyl]-m-xylene-α,α'diol (Salmeterol)

(w) N,N-dimethyl-N-(3-sulphopropyl)-4-[2[2-(2,3-dihydro-5-hydroxy-3-oxo-4H-1,4-benzoxazin-8-yl]-2,2-dimethylethyl]phenoxyammonium-hydroxide-hydrochloride monohydrate . $H_2O$ [internal salt]

(x) 5,5'-(2-hydroxy-trimethylenedioxy)-bis(4-oxo-chromen-2-carboxylic acid (Cromoglycinic acid)

(y) 9-ethyl-6,9-dihydro-4,6-dioxo-10-propyl-4H-pyrano[3,2-g]quinoline-2,8-dicarboxylic acid (Nedocromil)

Charging is conveniently carried out by dissolving the biodegradable polymer and the pharmaceutical substance in suitable solvents.

Examples include: ethers such as glycoldimethyl-ether, tetrahydrofuran and dioxan, ketones such as acetone, amides such as dimethylformamide or chlorinated hydrocarbons such as dichloromethane or chloroform or mixtures of solvents.

Suitable solvents for the biodegradable polymer or copolymer are those known from the prior art provided that they are inert with respect to the drug in question.

Suitable solvents for polylactides include halogenated hydrocarbons, preferably chlorohydrocarbons; dichloromethane is particularly preferred for poly-L(-)-lactide.

Suitable solvents for the drug include all inert solvents which will not react harmfully either with the drug or with the biodegradable polymer and which can be removed from the pharmaceutical preparation without any problems. Examples include halogenated hydrocarbons such as chloroform, methylene chloride (dichloromethane) or ketones such as acetone or ethylmethylketone or ethers such as glycoldimethylether or tetrahydrofuran. Obviously, mixtures of solvents may be used as the solvent both for the biodegradable polymer and for the drug.

It is also possible to include other excipients in the solution of the biodegradable polymer or in the solution of the drug.

Excipients which may be used include, in particular, antistatic agents such as soya lecithin, to make the grinding process easier and prevent electrostatic agglomeration of the particles.

Other adjuvants which may be used may include odour-masking substances which will if necessary mask the inherent smell of the drug or pharmacologically acceptable stabilisers or preservatives.

The micronised biodegradable particles are produced according to the invention by combining first of all a solution of the biodegradable polymer (optionally with excipients) and a solution of the drug, which may also contain other excipients desired.

It is, however, also possible to combine all the ingredients in one solution from the beginning, if a single solvent is used for both polymer and drug.

The solvent is removed from the resulting mixture, optionally under reduced pressure, depending on the boiling points of the solvent used and the thermal sensitivity of the drug.

The resulting solid material is pre-ground if necessary after drying and then subjected to jet grinding, to produce particles which have an average diameter on the order of 1 to 10 $\mu$m. Jet grinding has the further advantage that the temperature at which the grinding operation takes place can be regulated within wide limits, and this has the advantage, with respect to the ground material, that polymers which would be unsuitable for jet grinding becuase of their crystalline properties or hardness can optionally be comminuted at low temperatures to produce particles of the desired size. The process of jet grinding is known from the prior art [Ullmann's Encyclopedia of Industrial Chemistry, Vol. B2: Unit Operations I, VCH Verlagsgesellschaft mbH, D-6940 Weinheim, page 5–30 ff].

The method of production according to the invention results in micronised biodegradable particles in the form of an inhalable powder which can be used as a delayed release aerosol, even without the need for propellant gas (for example, the powder can be packed into a hard gelatine capsule and inhaled by the patient using a suitable inhaling device).

The biodegradable particles according to the invention may also be used in the form of injectable solutions, more particularly in preparations which are intended for intramuscular or intraarticular injection. The particular advantage of using the catalyst-free particles according to the invention, e.g. in intraarticular injection, is that the drug can be released in the desired target area without any local irritation being caused to the surrounding tissue by the polymer deposited or, in the case of a prolonged period of treatment, by the accumulation of catalyst residues.

The biodegradable particles according to the invention are also suitable for oral administration, e.g. in capsule form. Uniform release of the active substance over a long period of time can also be expected with this form of administration, since it can be assumed that the capsule contents will be well distributed in the intestines (the mixing ratio of the micronised particles with the food slurry may be equated, as a first approximation, with that of a liquid).

As for the drugs which may be used, the pharmaceutical compositions mentioned above may be supplemented with pharmaceutically active substances such as antiphlogistics or cytostatics, depending on the particular indication.

The micronised particles produced with poly-L(-)-lactide as the biodegradable polymer and fenoterol as the drug show, by their release characteristics in vitro and in vivo, that controlled release over several hours can be achieved with the particles according to the invention.

2. EXAMPLE OF APPLICATION

The Example which follows illustrates the invention without restricting it:

2.1. For these experiments, fenoterol base was used as the drug and poly-L(-)-lactic acid with a molecular weight of 2000 was used as the biodegradable polymer.

Soya lecithin was also included as an antistatic agent. Methylene chloride and acetone p.a. were used as organic solvents.

The quantities used in a typical example are shown in Table 1.

TABLE 1

| Quantity | Substance |
|---|---|
| 50 g | Poly-L(−)-lactic acid |
| 2.50 g | Fenoterol base |
| 1.5 g | Soya lecithin |
| 200 g | Methylene chloride |
| 100 g | Acetone |

The method used was to dissolve the poly-L(-)-lactic acid and soya lecithin in methylene chloride and, in a different container, the fenoterol base in acetone. The two solutions were then combined, the solvent was removed and then dried for 18 hours at 40° C. on a rack in a drying cupboard. After the drying process a white material was obtained which was first pre-ground with a mortar and then converted into a micronised powder by jet grinding (duration of grinding 3 minutes, grinding air at 5.5 atmospheres, air fed in at 5.0 atmospheres) using a 2" microniser by Sturtevent Mill Company Dorchester, Boston, Mass. Quantitative particle size analysis using a standard commercial particle size analyser showed that the average diameter $d_{3/50}$ was 2.4 μm.

TABLE 2

Particle size distribution of the jet-ground polylactide/fenoterol powder (HIAC method of measurement)

| Diameter in μm | Percentage of volume |
|---|---|
| 1.1 | 0.63 |
| 1.3 | 6.83 |
| 1.8 | 25.13 |
| 2.1 | 38.59 |
| 2.5 | 55.70 |
| 2.9 | 68.01 |
| 3.5 | 80.54 |
| 4.8 | 89.37 |
| 6.7 | 93.55 |
| 9.4 | 95.15 |

The release of fenoterol from the polymer carrier was determined in a Paddle Tester (USP XXI) in 0.05% aqueous benzalkonium chloride solution (T=21° C., stirrer speed 200 rpm). These in vitro process parameters were set so that it was possible to differentiate the rate of release between experimental formulations. The fenoterol was determined using the HPLC method. For the pharmacological inhalation experiments the desired quantity of micronised powder (e.g. for 200 μg of fenoterol HBr=4.32 mg in total) was weighed out and transferred into hard gelatine capsules. The dispersion and hence supply of the powder in the animal experiments were carried out by means of an inhalation device, and the aerosol produced in the animal experiment was directed straight into the trachea (modified method of Konzett and Rössler)

2.2. Quantities released, in %, of a formulation with a level of charging (active substance/polymer) of 4.6% and 2.4%

TABLE 3

| | Quantities released in % | |
|---|---|---|
| Release time in min. | 4.6% charging level | 2.4% charging level |
| 15 min. | 54.2% | 44.4% |
| 60 min. | 65.7% | 51.8% |
| 120 min. | 70.9% | 59.6% |
| 240 min. | 75.7% | 62.7% |

2.3. Animal-experimental method of determining the bronchospasmolytic effect on anaesthetised guinea-pigs The method of Gjurisch et al. [F. Gjurisch, B. Heike and E. Westermann, Naunyn-Schmiedeberg's Arch. exp. Pathol. Pharmakol. 247 (1964), 429] was modified. The animals used in the experiments were female albino guinea-pigs (Pirbright White, Ivanovas, fed with Sniff, body weight 300–400 g).

The animals were anaesthetised with 1.8 g/kg of ethyl urethane (as a 25% aqueous solution) i.p. Then, they were then subjected to tracheotomy and cannulation of the jugular vein. 3 mg/kg of Flaxedil i.v. was used for muscle relaxation. The guinea-pigs were connected to a ventilator for small animals: stroke volume 5 ml, frequency 60 strokes per minute, ventilation pressure kept constant at 10 ml of water column by means of a water excess pressure valve provided in the lateral connection (Konzett and Rössler). The body temperature was kept constant at about 38° C. (heating with a temperature sensor connected to an electronic temperature regulator). The tidal volume was measured in a body lethysmograph (diameter 9.7 cm, length 28.5 cm, internal height 8.3 cm, airtight seal provided by a glass plate, connections for ECG electrodes and a catheter for i.v. injection). For administration by inhalation, one stroke of the aerosol (delayed release formulation or fenoterol-glucose aerosol) was administered directly into the trachea. During administration, the connection between the trachea (or tracheal tube) and Fleisch tube (size 0000 for small animals) was briefly broken. Changes in the respiration pressure were detected by means of an electronic pressure transducer and recorded using a pen recorder. After a 30 minute settling down period the experiment was started. In order to initiate the bronchospasms, 30–50 μg/kg of acetyl choline was injected intravenously at 10 minute intervals until uniform bronchospasms (with the last two applications) could be detected. Then the test formulations were administered by inhalation and the spasmogens were injected intravenously at 10 minute intervals. The test results are shown in FIG. 1:

FIG. 1 shows the percentage inhibition of acetyl-choline-induced bronchospasm as a function of time.

Curve A: charging level 2.4%
Curve B: charging level 4.6%
Curve C: fenoterol-glucose aerosol As the biometry shows, the maximum effects between the delayed release aerosols containing poly-L(-)-lactic acid with charges of 2.4% and 4.6% (curves A and B, respectively) as against a fenoterol-glucose aerosol (curve C) are comparable in the first 15 minutes, but after this time the functions show a significantly different pattern, the preparation with 2.4% fenoterol giving the best results in terms of delayed release.

2.4 Further examples of application

Analogously to the method described above, pharmaceutical preparations were produced having a salbutamol base and ipratropium bromide. Drying, working up and grinding of the material were carried out under the same conditions as described hereinbefore for the preparation with the fenoterol base.

The particle size distribution, which was again determined by the HIAC method of measurement, is in the same range as that described for the fenoterol/polylactic acid system.

The release rates for the active substance in question were also determined under the same conditions as described for fenoterol base hereinbefore. For analytical determination, the HPLC method was used:

2.4.1 Salbutamol preparation

| Composition: | |
|---|---|
| 50 g | poly-L-lactic acid |
| 2.5 g (1.25 g) | salbutamol |
| 1.5 g | soya lecithin |
| 200 g | dichloromethane |
| 100 g | ethanol |

| | Amount released in %: | |
|---|---|---|
| Release Time in minutes | 4.6% charge | 2.4% charge |
| 15 | 63.3 | 52.3 |
| 60 | 71.1 | 56.0 |
| 120 | 74.2 | 60.3 |
| 240 | 75.3 | 69.9 |

2.4.2 Ipratropium preparation

| Composition | |
|---|---|
| 50 g | poly-L-lactic acid |
| 2.5 g | ipratropium bromide |
| 1.5 g | soya lecithin |
| 200 g | dichloromethane |
| 100 g | ethanol |

| Amount release in %: | |
|---|---|
| Release time in minutes | 4.6% charge |
| 15 | 53.6 |
| 60 | 58.0 |
| 120 | 61.1 |
| 240 | 67.0 |

We claim:

1. Micronized particles suitable for inhalation comprising an active pharmaceutical substance which particles are made by solubilizing a poly-L(-)lactide having a molecular weight in the range from about 1000 to about 10,000 with an active pharmaceutical substance, removing the solvent and then jet grinding the resulting solid material to produce particles having an average diameter of about 1 μm to about 10 μm.

2. The micronized particles according to claim 1 wherein the poly-L(-)-lactide has a molecular weight of from about 1000 to about 5000.

3. The micronized particles according to claim 1 wherein the active pharmaceutical substance is selected from the group consisting of anticholinergics, antiallergics, steroids and β-sympathomimetics.

4. The micronized particles according to claim 1 wherein the poly-L(-)-lactide has a molecular weight of from about 1000 to about 5000 and the active pharmaceutical substance is fenoterol.

5. Micronized particles suitable for inhalation comprising an active pharmaceutical substance which particles are made by solubilizing a biodegradable polymer having a molecular weight of from about 1000 to about 10,000 with an active pharmaceutical substance, removing the solvent and then jet grinding the resulting solid material to produce particles having an average diameter of about 1 μm to about 10 μm.

6. The micronized particles according to claim 5 wherein the biodegradable polymer is a hydroxycarboxylic acid selected from the group consisting of glycolide, lactide, methyl-glycolide, dimethylglycolide, diethyglycolide and dibutylglycolide.

7. The micronized particles according to claim 6 wherein the biodegradable polymer has a molecular weight of from about 1,000 to about 5,000.

* * * * *